United States Patent [19]

Misaki et al.

[11] Patent Number: 4,965,347
[45] Date of Patent: Oct. 23, 1990

[54] BETA-D-GLUCAN, AND ITS PRODUCTION AND USES

[75] Inventors: Akira Misaki, Hyogo; Yoshiaki Sone, Osaka; Masakazu Mitsuhashi; Toshio Miyake, both of Okayama, all of Japan

[73] Assignee: Kabushiki Kaisha Hayashibara Seibutsu Kagaku Kenkyujo, Okayama, Japan

[21] Appl. No.: 19,186

[22] Filed: Feb. 25, 1987

[30] Foreign Application Priority Data

Mar. 3, 1986 [JP] Japan .................................. 61-44189

[51] Int. Cl.$^5$ ..................... C07G 3/00; C08B 37/00; A61K 31/70; A61K 31/705
[52] U.S. Cl. ...................................... 536/1.1; 514/54; 435/74
[58] Field of Search ............................ 536/1.1; 514/54

[56] References Cited

U.S. PATENT DOCUMENTS

| | | | |
|---|---|---|---|
| 3,856,775 | 12/1974 | Fukuoka et al. | 536/1.1 |
| 3,893,996 | 7/1975 | Hamuro et al. | 536/1.1 |
| 4,225,673 | 9/1980 | Sugiura et al. | 435/101 |
| 4,398,023 | 8/1983 | Miyachi et al. | 536/1.1 |
| 4,454,289 | 6/1984 | Nakajima et al. | 536/1.1 |
| 4,454,315 | 6/1984 | Sasaki et al. | 536/18.2 |
| 4,639,516 | 1/1987 | Misaki et al. | 536/123 |
| 4,769,363 | 9/1988 | Misaki et al. | 514/54 |
| 4,774,093 | 9/1988 | Provonchee et al. | 424/493 |

FOREIGN PATENT DOCUMENTS 0121146 10/1984 European Pat. Off. .

OTHER PUBLICATIONS

Misaki, Akira, M. Kakuta, T. Sasaki, M. Tanaka, and H. Miyaji, "Studies on Interrelation of Structure and Antitumor Effects of Polysaccharides: Antitumor Action of Periodate-Modified, Branched (1-3)-β-D-Glucan of *Auricularia auricula-judae,* and Other Polysaccharides Containing (1-3) Glycosidic Linkages," Carbohydrate Research, vol. 92, pp. 115-129, 1981.

Patent Abstracts of Japan, vol. 10, No. 131 (C-346) [2188], May 15, 1986.

Acta Chemica Scandinavica, vol. 21, part III, No. 9, Sep. 1967, pp. 2379-2382, Copenhagen.

Agricultural and Biological Chemistry, vol. 50, No. 9, Sep. 1986, pp. 2171-2183, Tokyo, Japan.

*Primary Examiner*—John W. Rollins
*Assistant Examiner*—Gary L. Kunz
*Attorney, Agent, or Firm*—Browdy and Neimark

[57] ABSTRACT

Disclosed is a novel beta-D-glucan derived from a microorganism of the genus Aureobasidium. The beta-D-glucan exhibits physiological activities such as an activity of accelerating excretion of heavy metals, anticholesteremic-activity, and an antioncotic-activity via the cellular immune system.

3 Claims, 1 Drawing Sheet

BETA-D-GLUCAN, AND ITS PRODUCTION AND USES

BACKGROUND OF THE INVENTION

1. Field of the invention

The present invention relates to a novel beta-D-glucan, and its production and uses, for example, in chemicals, foods and pharmaceuticals.

2. Definitions

In the specification, parts and percentages will be expressed by weight based on the dry solid, unless specified otherwise, and Glc will mean beta-linked D-glucopyranose residue.

3. Description of the prior art

Certain beta-D-glucans have drawn attention as pharmaceuticals or ingredients thereof because the glucans show physiological activities such as blood-sugar lowering- and anti-cholesteremic-activities, and an antioncotic-activity via the cellular immune system.

Particularly, those beta-D-glucans that exhibit an antioncotic-activity to malignant tumors have drawn attention as antionotic agents: for example, pachyman reported by H. Saito et al., *Agricultural Biological Chemistry*, Vol.32, pp.1261-1269 (1968); lentinan reported by T. Sasaki and N. Takasuka, *Carbohydrate Research*, Vol.47, pp.99-104 (1976); schizophyllan reported by K. Tabata et al., *Carbohydrate Research*, Vol 89, pp.121-135 (1981); and the beta-D-glucan reported by A. Misaki et al., *Carbohydrate Research*, Vol.92, pp.115-129 (1981).

Since these beta-D-glucans are prepared from the fruit body of a microorganism of the class *Basidiomycetes*, these beta-D-glucans require a long preparation time and result in an insufficient yield.

BRIEF DESCRIPTION OF THE ACCOMPANYING DRAWING

FIG. 1 shows the infrared spectrum of the beta-D-glucan according to the invention.

DETAILED DESCRIPTION OF THE INVENTION

Figure 1:
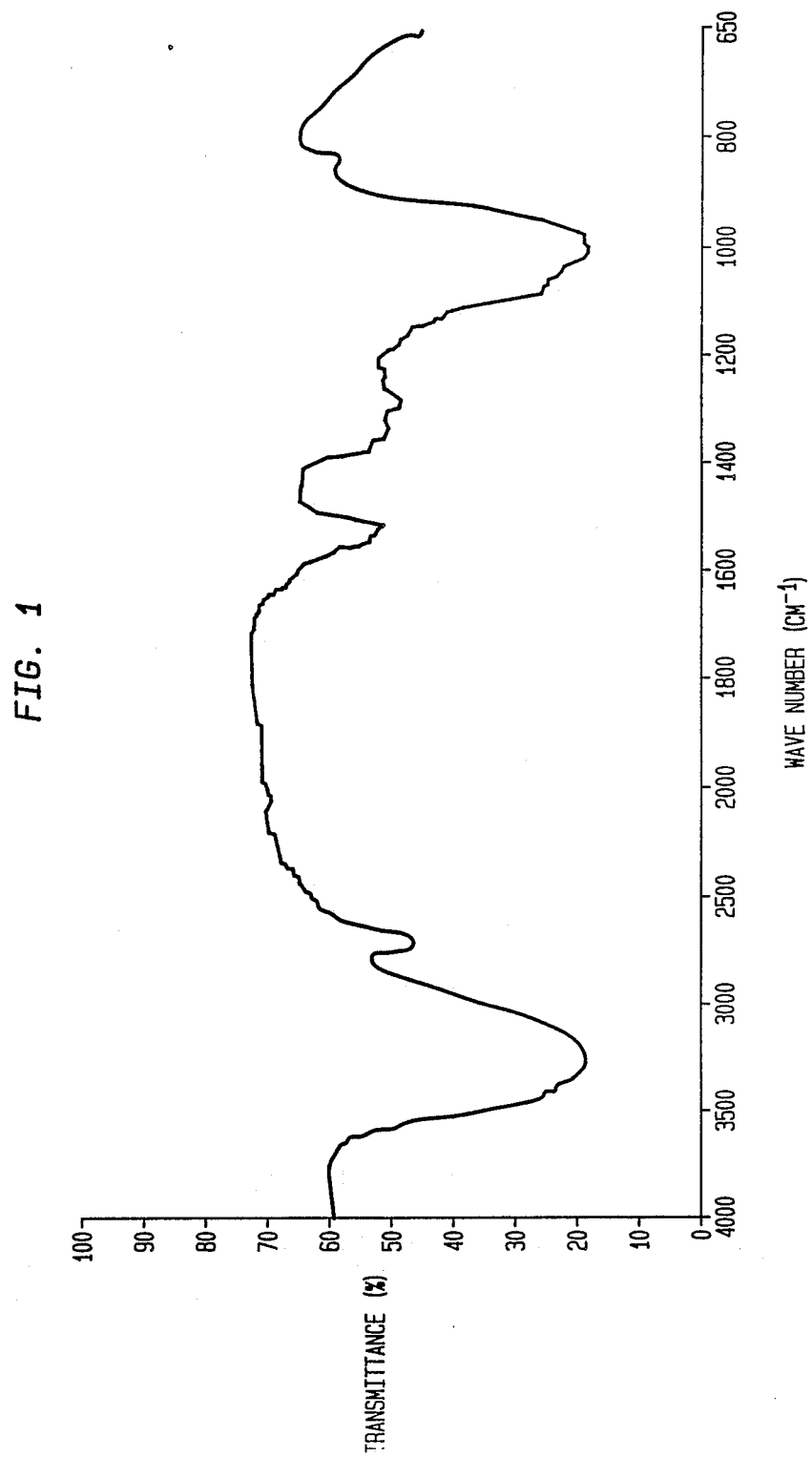

The present inventors studied beta-D-glucans which can be extensively used, for example, in pharmaceuticals, foods and chemicals.

As the result, the present inventors found in a culture of the genus Aureobasidium a novel beta-D-glucan having the following physicochemical properties:

| C ≈ 44.1% | H ≈ 6.18% |
|---|---|
| N < 0.1% | Ash < 0.01% |

(b) Molecular weight (by gel filtration); 100,000 to 500,000 daltons (c) Melting point: decomposable at about 230° C.

(d) Specific rotation $[\alpha]_D^{25}$; ±4 degrees (l=1, c=1.0%, 1 N NaOH)

(e) Infrared spectrum (by the KBr tablet method) as illustrated in FIG. 1

(f) Solubility; readily soluble in both 0.5 N NaOH and dimethyl sulfoxide: soluble in water: and insoluble in methanol, ethanol, acetone and chloroform (g) Color reaction;
anthrone-sulfuric acid reaction: positive
phenol-sulfuric acid reaction: positive
carbazole reaction: negative
ninhydrin reaction: negative
iodine reaction: negative (h) Properties in aqueous solution: 0.1% aqueous solution of a lyophilized preparation is neutral or slightly acidic (i) Appearance; white powder More particularly, the present inventors found that methylation analysis of the beta-D-glucan gave molecular ratios of 11 to 15 for 2,4,6-tri-O-methyl-D-glucose, 0.8 to 1.2 for 2,3,4-tri-O-methyl-D-glucose, 0.6 to 1.0 for 2,3,6-tri-O-methyl-D-glucose, and 0.8 to 1.2 for 2,4-di-O-methyl-D-glucose against 1.0 mole of 2,3,4,6-tetra-O-methyl-D-glucose: or, 3 to 5 for 2,4,6-tri-O-methyl-D-glucose, 0.3 to 0.5 for 2,3,4-tri-O-methyl-O-glucose, 0 2 to 0.4 for 2,3,6-tri-O-methyl-D-glucose, and 0.9 to 1.2 for 2,4-di-O-methyl-D-glucose against 1.0 mole of 2,3,4,6-tetra-O-methyl-D-glucose.

These findings confirmed that the beta-D-glucan was totally different from the polysaccharide that is derived from *Aureobasidium pullulans* as reported in R. G. Brown and B. Lindberg, *Acta Chemica Scandinavic* Vol.21, pp.2383-2389 (1967). The present inventors named this novel beta-D-glucan as "Aureobasillan".

The following further confirmed this:

(a) Element analysis:

| observed | C ≈ 44.1% | H ≈ 6.18% |
|---|---|---|
|  | N < 0.1% | Ash < 0.01% |
| calculated | C = 44.4% | H = 6.17% |

(b) Molecular weight (by gel filtration): 100,000 to 500,000 daltons (c) Melting point: decomposable at about 230° C.

(d) Specific rotation $[\alpha]_D^{25}$; ±4 degrees (l=1, c=1.0%, 1 N NaOH)

(e) Infrared spectrum (by the KBr tablet method): as illustrated in FIG. 1

(f) Solubility: readily soluble in both 0.5 N NaOH and dimethyl sulfoxide, soluble in water and insoluble in methanol, ethanol, acetone and chloroform (g) Color reaction;
anthrone-sulfuric acid reaction: positive
phenol-sulfuric acid reaction: positive
carbazole reaction: negative
ninhydrin reaction: negative
iodine reaction: negative (h) Properties in aqueous solution: 0.1% aqueous solution of a lyophilized preparation is neutral or slightly acidic (i) Appearance; white powder (j) Sugar components; Aureobasillan was completely hydrolyzed by subjecting it to an inorganic or organic acid, for example, in 72% sulfuric acid at ambient temperature for 5 minutes, diluting the mixture with 7 volumes of water, and incubating it at 100° C. for 4 to 5 hours: or by heating it at 100° C. for 6 hours in 2 M trichloroacetic acid. The resultant saccharide was analyzed by the paper chromatography, gas chromatography or glucose-oxidase/peroxidase method, and the resultant saccharide was D-glucose.

(k) Linkage:
(i) The low specific rotation $[\alpha]_D^{25}$, i.e., ±4 degrees, and the infrared absorption at about 890 cm$^{-1}$ indicate that all or most of the glucose residues constructing Aureobasillan are linked in beta-fashion.

(ii) Methylation analysis of Aureobasillan was carried out as follows: Aureobasillan was methylated in dimethylsulfoxide solution in accordance with the Hakomori method using methylsulfinyl carbanion and methyl iodide. The resultant methyl derivatives were acid-hydrolyzed, and then converted into alditol acetate. The gas chromatography and gas chromatography-mass spectrometry revealed that the alditol acetate had the following molecular ratios. An Aureobasillan specimen (Aureobasillan A) which had a relatively low molecular weight and did not adsorb onto DEAE-cellulose showed molecular ratios of 11 to 15 for 2,4,6-tri-O-methyl-D-glucose; 0.8 to 1.2 for 2,3,4-tri-O-methyl-D-glucose: 0.6 to 1.0 for 2,3,6-tri-O-methyl-D-glucose: and 0.8 to 1.2 for 2,4-di-O-methyl-D-glucose, against 1 mole of 2,3,4,6-tetra-O-methyl-D-glucose. The other Aureobasillan specimen (Aureobasillan B) which had a relatively high molecular weight and did not adsorb onto DEAE-cellulose showed molecular ratios of 3 to 5 for 2,4,6-tri-O-methyl-D-glucose: 0.3 to 0.5 for 2,3,4-tri-O-methyl-D-glucose; 0.2 to 0.4 for 2,3,6-tri-O-methyl-D-glucose; and 0.9 to 1.2 for 2,4-di-)-methyl-D-glucose, against 1.0 mole of 2,3,4,6-tetra-O-methyl-D-glucose.

(iii) A water-insoluble polymer fraction obtained by the moderate Smith degradation of Aureobasillan was methylated and acid-hydrolyzed to obtain a mixture of relatively large amount of 2,4,6-tri-O-methyl-D-glucose and a small amount of 2,3,4,6-tetra-O-methyl-D-glucose. The mixture was subjected to the action of an endo-type beta-1,3-glucanase to obtain a product which contained mainly, laminaribiose, and small amounts of glucose and $^2$6-O-beta-glucosyllaminaribiose. These facts showed that a substantial part of the beta-1,6 linkages was incorporated, adjacently to a beta-1,3 linkage, in the main chain which was repeatedly linked in beta-1,3 fashions.

These facts revealed that Aureobasillan was entirely different from conventional beta-D-glucans, based on the facts that it had beta-1,6 linkages at a constant ratio in the main chain which was repeated in beta-1,3 linkages and had short side chains which were branched at a constant ratio at the C-6 positions of the glucose residues; and that the side chains contained a substantial amount of beta-1,4 linkages in addition to beta-1,6 linkages.

Thus, Aureobasillan includes Aureobasillan A which is composed of the repeating units as represented by the following formulas:

FORMULA I

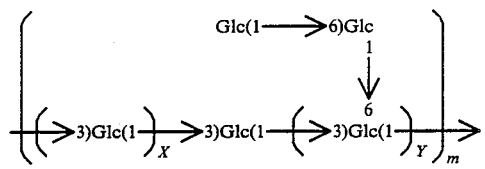

FORMULA II

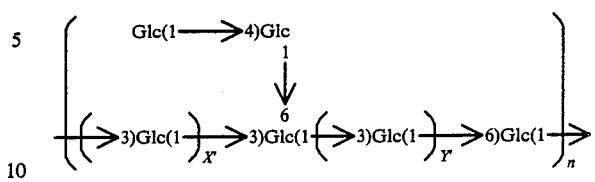

where X, Y, X' and Y' are 1 or larger integers, where X+Y and X'+Y' are integers in the range of from 11 to 15, and where m:n is from 1:3 to 1:5, and the Aureobasillan also includes Aureobasillan B which is mainly composed of the repeating units as represented by the following formulas:

FORMULA I

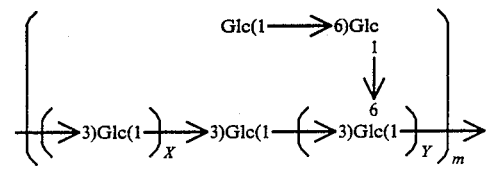

FORMULA II

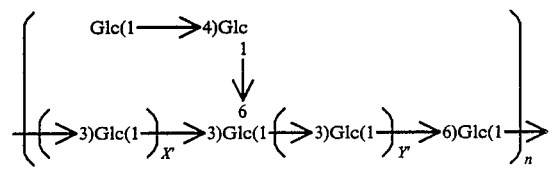

where X, Y, X' and Y are 1 or larger integers, where X+Y and X'+Y' are integers in the range of from 3 to 5, and where m:n is from 1:3 to 1:5.

To prepare Aureobasillan, a seed culture of, for example, *Aureobasidium pullulans* IFO 4464, IFO 4875, IFO 6353, IFO 6401, IFO 6725 or *Aureobasidium mansoni* IFO 9233 is inoculated to a solid culture medium or liquid culture medium, containing appropriate nutrients such as carbon source, nitrogen source and minerals, and the mixture was subjected to a static culture or submerged culture or shaking culture to accumulate Aureobasillan in the culture, followed by recovery of the accumulation.

Pullulan can be favorably accumulated in the culture along with Aureobasillan.

Any substance can be used as the nutrient in the culture medium as far as Aureobasillan is produced in the culture medium: for example, glycerol, xylose, glucose, sorbitol, fructose, maltose, isomaltose, maltitol, sucrose, lactose, cellobiose, maltotriose, maltotetraose, partial starch hydrolysates having a DE (dextrose equivalent) of 10 to 70, and exhausted molasses can be favorably used as the carbon source. To produce Aureobasillan and pullulan simultaneously, cultivation is favorably carried out with a liquid culture medium containing about 3 to 20 w/v % of one or more of these above saccharides under aerobic conditions. The synthetic compounds, such as, nitrate, ammonium salt and urea; and natural organic compounds, such as, polypeptone, yeast extract, malt extract, corn steep liquor, extract of defatted soybean, peptide, and amino acid can be favorably used as the nitrogen source.

The mineral(s) may be selected from one or more of phosphate, potassium salt, sulphate, magnesium salt, and, if necessary, ferrate, manganate, and calcium salt.

The pH and temperature during cultivation are those under which the microorganism grows and produces Aureobasillan: generally, pH 2.0 to 9.0 and temperature 15 to 35° C. The cultivation is continued until Aureobasillan production maximizes: generally 1 to 10 days in the case of using a liquid culture medium under aeration-agitation conditions.

Aureobasillan can be recovered from the culture, for example, by collecting the cells from the culture, and separating the Aureobasillan from the cells. Pullulan can be recovered by conventional procedure from the cell-free filtrate or supernatant of the culture.

Aureobasillan can be recovered from the cells by allowing cell-walls derived from cells or cell debris to contact with an eluent, for example, hot water, dilute acid or dilute alkali, particularly, an aqueous alkaline solution of a pH exceeding 7.0, more particularly, 0.01 to 4.0 N dilute aqueous solution of potassium hydroxide, sodium hydroxide, magnesium hydroxide or calcium hydroxide, to elute the Aureobasillan, followed by recovery of the Aureobasillan solution.

The Aureobasillan solution is, if necessary, after concentration, neutralization, decoloration, deionization and purification with an activated carbon and ion-exchange resins in usual manner, concentrated and dehydrated to obtain a white Aureobasillan powder.

An ultracentrifugally- and electrophoretically-homogeneous high-purity Aureobasillan fraction can be easily obtained by treating an aqueous Aureobasillan solution with an organic precipitant such as methanol, ethanol, isopropanol and acetone, or by chromatographying the aqueous solution.

The resultant high-purity Aureobasillan can be easily dehydrated and pulverized. To effect such dehydration, conventional method such as flow drying, hot air drying, spray drying, drum drying and lyophilizing can be chosen.

In order to prepare a polyol-type Aureobasillan from the Aureobasillan thus obtained, one part of the latter Aureobasillan is dissolved or suspended in about 50 to 500 parts aqueous solution containing about 0.01 to 0.5 M of periodic acid or periodate such as meta-sodium periodate and meta-potassium periodate, and allowed to react, generally, at a pH in the range of from 3 to 8. This operation is generally carried out under mild conditions, for example, at ambient temperature in the dark, particularly, at a temperature of 15° C. or lower in the dark for 1 to 5 days, to complete the oxidation reaction. The polyaldehyde-type Aureobasillan thus obtained wherein the side chains have been mainly oxidized can be advantageously used as the carrier for an immobilized enzyme by the covalent method because of the high reactivity.

In order to reduce the polyaldehyde-type Aureobasillan, the residual periodic acid in the reaction mixture is consumed with addition of ethylene glycol, or removed by dialysis, thereafter the resultant is reduced with a reductant. If necessary, polyaldehyde-type Aureobasillan may be recovered from the reaction mixture, prior to the reduction reaction.

Any reducing method can be employed as long as the oxidized Aureobasillan is reduced with: for example, hydrogenation using nickel catalyst and reduction using sodium borohydride may be chosen. The nickel catalyst in the reaction mixture is removed or the sodium borohydride in the reaction mixture is decomposed by the addition of an organic acid in usual manner. Then the reaction mixture is subjected to repeated precipitations using an organic precipitant, if necessary, decolored, deionized and purified with an activated carbon and ion-exchange resins, and concentrated to obtain a polyol-type Aureobasillan syrup which is easily preparable into powder. In the polyol-type Aureobasillan, the beta-1,3 linked glucose residues were left unchanged, but the remaining beta-1,6 linked glucose residues in the side chains were ring cleaved.

The intact and polyol-type Aureobasillans thus obtained can be freely used, for example, in chemicals, foods and pharmaceuticals. In the case of chemicals, intact Aureobasillan can be freely prepared alone or in combination with one or more materials into composition or shaped bodies, for example, granules tablets and sheets because intact Aureobasillan is a water soluble saccharide. Polyol-type Aureobasillan is suitable for sizing use as a agent, viscosity-imparting agent, emulsifier, fiber, film and coating membrane, because polyol-type Aureobasillan is a readily water soluble polysaccharide. In the case of foods, intact and polyol-type Aureobasillans can be favorably used in health promoting food because they are edible, non-toxic, tasteless, non- or hardly-assimilable fibers having an anticholesteremic-activity as well as an activity of accelerating excretion of heavy metals.

Intact and polyol-type Aureobasillans can be freely used in pharmaceuticals, in particular, antioncotic because they activate the cellular immune system to exhibit a high antioncotic-activity. Thus, intact and polyol-type Aureobasillans can be used alone or in combination with one or more agents and/or adjuvants, for example, in the form of injection or internal- or external-medicine in the therapy of malignant tumors which are sensitive to intact or polyol-type Aureobasillan, for example, breast cancer, lung cancer, bladder cancer, hysterocarcinoma, colorectal cancer, gastric cancer, leukemia, lymphoma and skin cancer.

The efficacy of such therapy may be augmented by a combined use with one or more other antioncotics, for example, alkylating agents such as cyclophosphamide and nimustine hydrochloride; antimethabolites such as methotrexate, fluorouracil and tegafur; antibiotics such as bleomycin, mytomycin C and actinomycin C; alkaloids such as vincristine sulfate and vinblastine sulfate; hormones such as prednisone, methyltestosterone and conjugated estrogen; and lymphokines such as interferon, lymphotoxin, tumor necrosis factor and interleukin 2.

The following experiments will illustrate the antioncotic-activity, toxicity, efficacy and dosage of intact and polyol-type Aureobasillans.

EXPERIMENT 1

Ten 4 week-old ICR-JCL female mice were implanted with about $6 \times 10^6$ cells of Sarcoma-180 tumor line into their right groins. From the first day following the implantation, 0.1 ml saline containing 1, 5 or 10 mg/kg mouse of either Aureobasillan, obtained by the method in Example 1, or a polyol-type Aureobasillan, obtained by the method in Example 3, was daily injected intraperitoneally into the mice 1 dose per day over a period of the following 10 days. As control, a saline free of the intact or polyol-type Aureobasillan was administered in the same manner. On the thirty-fifth day after the implantation, the tumors, formed in the animals, were extracted and weighed. The tumor inhibitory ratio (%) was determined by comparing the weight of the tumor of the group which was administered with the intact or polyol-type Aureobasillan with that of the control group.

$$\text{Tumor inhibitory ratio (\%)} = \frac{(A - B)}{A} \times 100$$

where A is the average tumor weight of the 10 control mice; and B, the average of the 10 mice which had been administered with the intact or polyol-type Aureobasillan.

The results were as shown in Table 1.

were weighed. The tumor inhibitory ratio (%) was determined in the same manner as in Experiment 1.

The results were as shown in Table 2.

TABLE 2

|  |  | Dose mg/kg/day × time | Average tumor weight (g) | Tumor inhibitory ratio (%) | Remarks |
|---|---|---|---|---|---|
|  |  | 0 × 10 × 2 | 8.4 ± 0.5 | — | control |
| Intact Aureobasillan | A | 0.02 × 10 × 2 | 5.7 ± 0.4 | 32.1 | present invention |
|  |  | 0.1 × 10 × 2 | 5.0 ± 0.6 | 40.5 | present invention |
|  |  | 1 × 10 × 2 | 3.9 ± 0.5 | 53.6 | present invention |
|  | B | 0.02 × 10 × 2 | 5.9 ± 0.5 | 29.8 | present invention |
|  |  | 0.1 × 10 × 2 | 5.1 ± 0.4 | 39.3 | present invention |
|  |  | 1 × 10 × 2 | 4.2 ± 0.6 | 50.0 | present invention |
| Polyol-type Aureobasillan | A | 0.02 × 10 × 2 | 5.3 ± 0.6 | 36.9 | present invention |
|  |  | 0.1 × 10 × 2 | 4.0 ± 0.7 | 52.4 | present invention |
|  |  | 1 × 10 × 2 | 2.9 ± 0.5 | 65.5 | present invention |
|  | B | 0.02 × 10 × 2 | 5.4 ± 0.6 | 35.7 | present invention |
|  |  | 0.1 × 10 × 2 | 4.2 ± 0.7 | 50.0 | present invention |
|  |  | 1 × 10 × 2 | 3.0 ± 0.6 | 64.3 | present invention |

These results revealed that intact and polyol-type Aureobasillans were very efficacious against malignant tumors, such as lung cancer, the therapy of which has been deemed very difficult.

EXPERIMENT 3

Both intact and polyol-type Aureobasillans, obtained by the method in Experiment 1 or 3, were tested their acute toxicity by administering either of them orally, intraperitoneally or intraveneously into 4 week-old mice by conventional method.

As the result, both beta-glucans were extremely low in toxicity, and their highest possible dosage resulted in no death of the mice. 1 The $LD_{50}$ (median lethal dose)

TABLE 1

|  |  | Dose mg/kg/day × time | Average tumor weight (g) | Tumor inhibitory ratio (%) | Number of mice completely involuted | Remarks |
|---|---|---|---|---|---|---|
|  |  | 0 × 10 × 1 | 9.6 ± 1.4 | — | 0 | control |
| Intact Aureobasillan | A | 1 × 10 × 1 | 0.3 | 96.9 | 9 | present invention |
|  |  | 5 × 10 × 1 | 0 | 100 | 10 | present invention |
|  |  | 10 × 10 × 1 | 0 | 100 | 10 | present invention |
|  | B | 1 × 10 × 1 | 0.4 | 95.8 | 9 | present invention |
|  |  | 5 × 10 × 1 | 0 | 100 | 10 | present invention |
|  |  | 10 × 10 × 1 | 0 | 100 | 10 | present invention |
| Polyol-type Aureobasillan | A | 1 × 10 × 1 | 0 | 100 | 10 | present invention |
|  |  | 5 × 10 × 1 | 0 | 100 | 10 | present invention |
|  |  | 10 × 10 × 1 | 0 | 100 | 10 | present invention |
|  | B | 1 × 10 × 1 | 0 | 100 | 10 | present invention |
|  |  | 5 × 10 × 1 | 0 | 100 | 10 | present invention |
|  |  | 10 × 10 × 1 | 0 | 100 | 10 | present invention |

These results revealed that intact and polyol-type Aureobasillans very effectively inhibited the growth of malignant tumors.

The data from this experiment have been deemed applicable to other warm-blooded animals, for example, mammalians such as human, cow, horse, dog, cat, rabbit and rat, and fowls such as chicken and pigeon.

EXPERIMENT 2

Ten BDF₁ male mice, about 25 g each, were implanted with a 2 mm-square of piece Lewis lung cancer tissue on their dorsal area. On the eighth day after the implantation, 0.1 ml saline containing 0.02, 0.1 or 1 mg/kg mouse of either intact or polyol-type Aureobasillan, obtained by the method in Example 1 or 3, was daily injected intraperitoneally into the mice at 2 doses per day over a period of the following 10 days. As control, a saline free of intact or polyol-type Aureobasillan was administered in the same manner. On the twenty-third day after the implantation, the tumors of both beta-D-glucans were, not necessarily correct, 20 g/kg or higher when orally administered: 5 g/kg or higher when intraperitoneally administered: and 1.5 g/kg or higher when intraveneously administered.

As is evident from these Experiments, intact and polyol-type Aureobasillans would be safe in view of their effective doses. Thus, intact and polyol-type Aureobasillans can be favorably used in the therapy of malignant tumors. Any administration method can be employed as long as it is effective in the therapy of malignant tumors: for example, subcutaneous-, intramuscular- or intravenous-injection: oral administration; suppository administration; external application: and instillation.

The dose of intact and polyol-type Aureobasillans for adult per day is generally 0.1 mg to 500 g, in particular, 10 mg to 500 g for oral administration, and 0.1 mg to 100 g for injection, but varies with the administration method employed.

Several embodiments according to the invention.

EXAMPLE 1

Aureobasillan

A seed culture of *Aureobasidium pullulans* IFO 4464 was inoculated in a 20 liters culture medium comprising 10% of partial starch hydrolysate (D.E.40), 0.2% of $K_2HPO_4$, 0.2% of peptone, 0.2% of NaCl, 0.04% of $MgSO_4$ heptahydrate and 0.001% of $FeSO_4$ heptahydrate, and the mixture was cultivated at 27° C. for 5 days under aeration-agitation conditions. The cells were separated with a precoated filter.

The resultant filtrate was purified, concentrated, and pulverized in usual manner to obtain about 1.4 kg of a pullulan powder.

The separated cells, about 200 g as the dry solid, were washed with hot water, fed to "Dino Mill", a cell crusher manufactured by Willy A. Bachofen, Basel, Switzerland, and centrifuged to collect the cell debris which was then defatted with acetone and added with 4 liters of 0.5 N sodium hydroxide. The mixture was then gently stirred in a nitrogen atmosphere at 25° C. for 4 hours, followed by centrifugation. The resultant supernatant was dialyzed against water, dehydrated and concentrated to obtain about 8 g of a crude Aureobasillan. One g of the Aureobasillan was dissolved in 200 ml of 0.01 M phosphate buffer (pH 7.8), and the resultant solution was applied on a column of DEAE-cellulose. The non-adsorbed fraction was then dialyzed, concentrated, lyophilized and pulverized to obtain about 400 mg of a white Aureobasillan A powder.

The molecular weight of the product was 100,000 to 200,000 daltons as determined by gel chromatography using a column of Sepharose CL-6B, registered trade mark of Pharmacia, Uppsala, Sweden.

The specific rotation $[\alpha]_D^{25}$ of 1.0% aqueous solution, prepared by dissolving the powder with 1 N sodium hydroxide in a nitrogen atmosphere, was plus one degree.

The infrared spectrum of the powder determined by the KBr tablet method was as shown in FIG. 1.

The fraction which had adsorbed onto the column of DEAE-cellulose was eluted with 0.1 N aqueous solution of sodium hydroxide, purified similarly as in the non-adsorbed fraction, and pulverized to obtain about 500 mg of an Aureobasillan B powder.

The molecular weight and specific rotation $[\alpha]_D^{25}$ of the Aureobasillan B powder, as determined similarly as with Aureobasillan A, were 350,000 to 450,000 daltons and minus one degree respectively. The infrared spectrum of the Aureobasillan B powder was approximately the same absorption pattern as shown in FIG. 1.

The Aureobasillans thus obtained can be favorably used in chemicals, foods and pharmaceuticals.

EXAMPLE 2

Twenty liters of a liquid culture medium, consisting of 8 w/v % of sucrose, 0.2 w/v % of yeast extract, 0.3 w/v % of corn steep liquor, 0.1 w/v % of $NH_4NO_3$, 0.1 w/v % of $K_2HPO_4$, 0.05 w/v % of $MgSO_4$ heptahydrate, 0.05 w/v % of KCl, 0.0001 w/v of $MnSO_4$ tetrahydrate and water, was sterilized at 120° C. for 20 minutes, cooled, adjusted to pH 7.0, and inoculated with a seed culture of *Aureobasidium pullulans* IFO 6353. The mixture was then cultivated at 30° C. for 4 days under aeration-agitation conditions. The resultant culture was treated similarly as in Example 1 to recover from the filtrate of the culture about 0.7 kg of a pullulan powder and, from the cell, about 7 g of a crude Aureobasillan.

One gram of the crude Aureobasillan was dissolved in 500 ml of 0.01 N aqueous sodium hydroxide solution, decolorized with an activated carbon, deionized and purified with ion-exchange resins (H- and OH-forms) in usual manner, concentrated, lyophilized and pulverized to obtain about 800 mg of a high-purity white Aureobasillan powder. The specific rotation $[\alpha]_D^{25}$ of the powder containing Aureobasillans A and B was zero degree.

Similar to the preparation obtained by the method in Example 1, the powder can be extensively used.

EXAMPLE 3

Polyol-type Aureobasillan

Ten grams of either Aureobasillan A or B, obtained by the method in Example 1, was suspended in 500 ml of an aqueous solution containing 6.6 g of meta-sodium periodate, and the mixture was then stirred at 10° C. in the dark for 7 days to effect oxidation. The reaction mixture was dialyzed against water. The liquid inside the dialyzing means was added with 1.5 g of sodium borohydride, and the mixture was allowed to effect reduction at ambient temperature for 2 days, and adjusted to pH 6.0 with acetic acid to decompose the remaining sodium borohydride. Thereafter, the resultant was dialyzed against water.

The liquid inside the dialyzing means was added with 3 volumes of methanol, and the resultant precipitate was centrifuged, dissolved in water, precipitated, dissolved in water, lyophilized and pulverized to obtain about 7.5 g of a pulverulent polyol-type Aureobasillan A or B.

The products are superior in water-solubility to intact Aureobasillan, and are favorably usable in chemicals, foods and pharmaceuticals.

EXAMPLE 4

Film

A 10 w/v % aqueous solution of a polyol-type Aureobasillan A, obtained by the method in Example 3, also containing glycerine in an amount of 10% against the dry solid of the polyol-type Aureobasillan A, was casted on a glass plate, and dehydrated with 70° C. air to obtain a film having a satisfactory transparency, brightness, and physical strength. Since the product exhibits a high oxygen-impermeability, it can be favorably used to coat or pack products which are suscepable to oxidation to prolong their storage period and shelf lives.

EXAMPLE 5

Fiber

A 20 w/v % aqueous solution of a polyol-type Aureobasillan B, obtained by the method in Example 3, was heated to 80° C., and extruded into fiber in the air at ambient temperature through a cylindrical nozzle 0.3 mm in diameter and 1 mm in length, pressure of 3 kg/cm², and the fiber was wound around a core.

The obtained fiber, thickness, about 20 μ, was satisfactory in physical strength. The fiber can be twisted, knitted or woven. The fiber is hydrophilic, non-toxic, and non-skin-irritative, so that the fiber can be favorably used, for example, as absorbent cotton, sanitary cotton, gauze, gut in therapy, or shaped body in therapy of malignant tumors. By utilizing the satisfactory moisture-absorbing ability, non-electrifiability, and stainability, the product can be used in blended fiber for clothes such as underwears.

EXAMPLE 6

Coating membrane

Fresh eggs, soaked in a 35° C. aqueous solution containing 0.5 w/v % of a crude Aureobasillan, obtained by the method in Example 2, for 30 seconds within 10 hours after the eggs had been laid, and dehydrated in a 30° C. air for 1 hour to form a coating membrane over the surface of the eggs, were stored at ambient temperature, i.e., 15 to 25° C., and their shelf lives were compared with those of uncoated control eggs. The results revealed that the coating kept the eggs fresh about 5 to 10 times longer than the uncoated control eggs.

EXAMPLE 7

Cup

An Aureobasillan A powder, obtained by the method in Example 1, was sprinkled with water to attain a moisture content of about 30% with mixing, and fed to an extruder to form a rod which was then cut into pellets, 25 mm in diameter, 4 mm in length. The pellets were then fed to an injection molder, and injected at a resin temperature of 120° C. to obtain

EXAMPLE 8

Fertilizer rod

Seventy parts of a compound fertilizer (N=14%, $P_2O_5$=8%, $K_2O$=12%), 10 parts of a crude Aureobasillan, obtained by the method in Example 1, 15 parts of calcium sulfate and 5 parts of water were sufficiently mixed, and heated to 80° C. in an extruder (L/D=20, compression ratio=18 and dice diameter=30 mm) to obtain a fertilizer rod.

The product is convenient to carry and does not necessarily require a container. The product has a physical strength sufficiently for total layer application, and the releasing ratio can be controlled by varying the formulation of the components in the compound fertilizer.

EXAMPLE 9

Capsule

An aqueous solution of 5 w/v % polyol-type Aureobasillan A, obtained by the method in Example 3, and 10 w/v % of gelatin was heated to 60° C., and degassed. The end of a metal rod was soaked in the solution, immediately pulled out, and dehydrated gradually in a 40° C. air to obtain a high-quality hard capsule having a satisfiable elasticity, transparency and brightness. The product can be favorably used for packaging, for example, a suppository and a medicament for oral administration.

EXAMPLE 10

Adhesive

A mixture of 30 parts of dimethylsulfoxide, 25 parts of water, 2 parts of a high-purity Aureobasillan, obtained by the method in Example 2, 8 parts of pullulan, and 2 parts of dibenzylidene xylitol was dissolved by 1 hour-stirring at 90° C., injected into a cylindrical lipstick-type container, 14 mm in diameter, 50 mm in height, equipped with an up and down moving mechanism, and cooled at ambient temperature to obtain a solid-type adhesive. The adhesive can be applied on a kraft to form a layer of uniform thick on the paper, and the adhesive also exhibits a sufficient initial adhesion.

EXAMPLE 11

Alimentary pastes

Seventy parts of rice powder, 20 parts of potato starch, 10 parts of wheat flour, 2 parts of an Aureobasillan A, obtained by the method in Example 1, and 40 parts of 10% aqueous saline solution were homogeneously mixed, steamed, sufficiently kneaded, and prepared into a dough, followed by overnight standing. The resultant was cut into alimentary pastes, and placed in boiling water for 3 minutes, The alimentary pastes had a sufficient "koshi (softness and chewiness)".

EXAMPLE 12

"Chinmi (a type of relish)"

A "soboro (a minced meat)", prepared by roasting with a frying pan 30 parts of minced chicken, 2 parts of sucrose, 2 parts of soy sauce and 6 parts of "mirin (sweet sake)", was added with 3 parts of an Aureobasillan B powder, obtained by the method in Example 1, sufficiently kneaded, pressed at about 50 kg/cm² while heating at about 150° to 170° C. to obtain about 1 cm thick sheets. The sheets were cut into pieces to obtain the captioned product having a delicate flavor. The product was suitable for relish or snack for children.

EXAMPLE 13

Fish paste product

Four thousand parts of a thawed walleye pollack paste was homogeneously grinded and kneaded with 80 parts of maltose, 80 parts of sodium glutaminate, 200 parts of potato starch, 300 parts of ice water, 12 parts of sodium tripolyphosphate, 120 parts of salt, and 100 parts of an aqueous solution obtaining 10 parts of a polyol-type Aureobasillan A, obtained by the method in Example 3, and 1 part of sorbitol. About 120 g aliquots bars were steamed in such manner that the products were heated up to about 80° C. over a period of 30 minutes. Then, the products were cooled at ambient temperature, and allowed to stand at 4° C. for 24 hours to obtain fish paste products.

These products had satisfactory gloss and biting properties.

EXAMPLE 14

"Koromo (batter)" for fried food

One part of a high-purity Aureobasillan, obtained by the method in Example 2, was added to 100 parts of weak flour, and the resultant mixture was admixed with 300 parts of water to obtain "koromo". "Tane (seafoods and vegetables for fried food)" such as lobster or sweet potato, was coated with the "koromo", and fried. The fried "koromo" had desirable biting properties and adhesion to "Tane".

EXAMPLE 15

Ice cream

Seventy parts of 40% cream, 200 parts of sweetened condensed milk, 460 parts of whole milk, 20 parts of skim milk, 5 parts of sucrose, 5 parts of maltose and 4 parts of 1.0 w/v % aqueous solution of a high-purity Aureobasillan, obtained by the method in Example 2, were mixed by heating and pasteurized at 70 ° C. for 30 minutes, cooled quickly to 3 to 4° C. with a homogenizer, aged overnight, and fed to a freezer.

The product was a tasty ice cream.

EXAMPLE 16

Lemon jelly

Three parts of agar and 5 parts of a polyol-type Aureobasillan B, obtained by the method in Example 3, were added with 200 parts of water and 50 parts of sucrose, and the mixture was dissolved by heating, and cooled to 65° C.

The mixture was then added with 350 parts of carbonated water containing small amounts of flavors including lemon flavor, and the resultant was poured into cups, and cooled to obtain a lemon jelly having a satisfiable gloss. The product is a health promoting food containing polyol-type Aureobasillan B which is an edible fiber.

EXAMPLE 17

Yoghurt

One hundred and seventy-five parts of a skim milk powder, 80 parts of sucrose, 50 parts of maltose, and 30 parts of an Aureobasillan A, obtained by the method in Example 1, were dissolved in 1,200 parts of water while stirring, and the mixture was fed to a homogenizer, pasteurized at about 85° C. for 30 minutes, and cooled to 40° C.

The mixture was added with 30 parts of a starter prepared with the lactic acid bacteria in commercialized yoghurt, and the resultant was cultured at 37° C. for 8 hours to obtain a yoghurt-gel.

The product was a tasty yoghurt having a smoothness and satisfiable gloss. The product is a health promoting food where Aureobasillan A provides an anticholesteremic-activity.

EXAMPLE 18

Tablet

One hundred parts of an aqueous solution of 20 w/v % polyol-type Aureobasillan A, obtained by the method in Example 3, was admixed with 140 parts of maltose, and 20 parts of vitamin A palmitate, and the mixture was sufficiently mixed, poured over a glass plate, and air-dried. Then, the resultant product was pulverized and fed to a tableting machine to prepare tablets according to conventional method. The tablet contained 100,000 IU vitamin A palmitate per gram, and, after 3-month standing at 30° C., no decrease in activity was noted. The product can be favorably used as an antioncotic which is orally administered for malignant tumors, for example, gastric cancer, duodenal cancer and rectal cancer.

EXAMPLE 19

Tablet

Fourteen parts of an Aureobasillan B, obtained by the method in Example 1, and 4 parts of corn starch were sufficiently mixed with 50 parts of salicylic acid, and the resultant mixture was tableted in a tableting machine in conventional method.

The product was non-hygroscopic, and sufficient in physical strength, as well as exhibiting a satisfiable disintegration in water.

EXAMPLE 20

Injection

An aqueous solution of 0.2 w/v % Aureobasillan A, obtained by the method in Example 1, was decolored with an activated carbon, deionized and purified with ion-exchange resins (H- and OH-forms), concentrated and sterilized with a membrane filter. The filtrate was distributed into sterilized 20 ml glass-vials containing 200 mg Aureobasillan A, and lyophilized to obtain an injection. The product can be, after dissolving or suspending the Aureobasillan A in saline, favorably injected subcutaneously or intramuscularly in the therapy of malignant tumors, for example, breast cancer, lung cancer, hepatoma and leukemia.

EXAMPLE 21

Injection

An aqueous solution of about 2 w/v % polyol-type Aureobasillan B, obtained by the method in Example 3, was decolored with an activated carbon, deionized and purified with ion-exchange resins, concentrated and sterilely filtered with a membrane filter similarly as in Example 20. The filtrate was prepared into 2 w/v % isotonic solution of polyol-type Aureobasillan B, which was then distributed into 20 ml vials to obtain an injection.

The product can be favorably injected intraperitoneally or intravenously for treating malignant tumors, for example, breast cancer, bladder cancer, hysterocarcinoma, colorectal cancer and gastric cancer.

EXAMPLE 22

Ointment

A high-purity Aureobasillan powder, obtained by the method in Example 2, was admixed with a small amount of liquid paraffin, and added with white petrolatum to obtain an ointment containing 10 mg Aureobasillan per gram.

The product can be favorably used for treating malignant tumors, for example, skin cancer, breast cancer and lymphoma.

As is apparent from the above, the present beta-D-glucan and its derivative, i.e., polyol-type Aureobasillan, can be favorably used in the form of a composition in a health promoting food because they are edible, tasteless, non-toxic and non- or hardly-assimilable fibers. In addition, intact and polyol-type Aureobasillans have an anticholesteremic-activity or an activity of excreting heavy metals. Intact and polyol-type Aureobasillans can be favorably used, for example, in an antioncotic for treating malignant tumors because of their antioncotic-activity: and in a shaped body or composition, for example, in the form of tablet, film, and sheet.

Preparation of Aureobasillan at an industrial-scale can be favorably carried out by culturing a microorganism of the genus Aureobasidium and recovering the accumulated Aureobasillan from the culture. The pullulan accumulated along with Aureobasillan can be favorably recovered from the culture.

It will be obvious to those skilled in the art that various changes and alternations may be made without departing from the scope of the invention and the invention is not to be considered limited to what is described in the specification.

We claim:

1. A beta D-glucan which has the following physicochemical properties:

(a) Element analysis;

C = 44.1%  H = 6.18%
N < 0.1%  Ash < 0.01%

(b) Molecular weight (by gel filtration); 100,000 to 500,000 daltons (c) Melting point; decomposable at about 20° C.

(d) Specific rotation $[\alpha]_D^{25}$; ± degrees (l=1, c=1.0%, 1 N NaOH)

(e) Infrared spectrum (by the KBr tablet method); as illustrated in FIG. 1

(f) Solubility; readily soluble in both 0.5 N NaOH and dimethyl sulfoxide; soluble in water; and insoluble in methanol, ethanol, acetone and chloroform (g) Color reaction;
anthrone-sulfuric acid reaction: positive
phenol-sulfuric acid reaction: positive
carbazole reaction: negative
ninhydrin reaction: negative
iodine reaction: negative (h) Properties in aqueous solution; 0.1% aqueous solution of a lyophilized preparation is neutral or slightly acidic (i) Appearance; white power;

and wherein, upon methylation analysis, said beta-D-glucan gives the molecular ratios of 11 to 15 for 2,4,6-tri-O-methyl-D-glucose; 0.8 to 1.2 for 2,3,4-tri-O-methyl-D-glucose, 0.6 to 1.0 to 2,3,6-tri-O-methyl-D-glucose; and 0.8 to 1.2 for 2,4-di-O-methyl-D-glucose against 1.0 mole of 2,3,4,6-tetra-O-methyl-D-glucosse; or, 3 to 5 for 2,4,6-tri-O-methyl-D-glucosse; 0.3 to b 0.5 for 2,3,4-tri-O-methyl-D-glucose; 0.2 to 0.4 for 2,3,6-tri-O-methyl-D-glucose; and 0.9 to 1.2 for 2,4,-di-O-methyl-D-glucose against 1.0 mole of 2,3,4,6-tetra-O-methyl-D-glucose.

2. The beta-D-glucan of claim 1, which is mainly composed of the repeating units selected from the group consisting of units represented by the following formulas:

FORMULA I

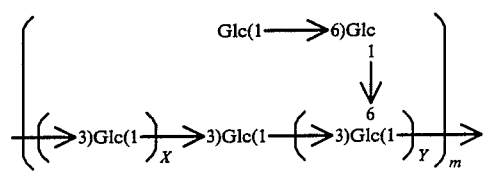

FORMULA II

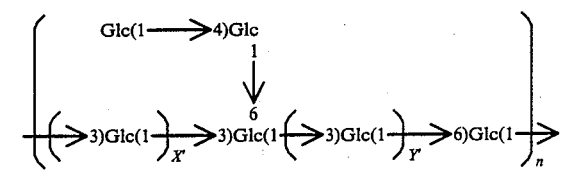

where X, Y, X' and Y' are 1 or larger integers, where X+Y and X'+Y' are integers in the range of from 11 to 15, an where m:n is from 1:3 to 1:5; and,

FORMULA III

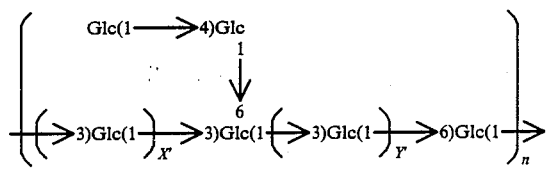

FORMULA IV

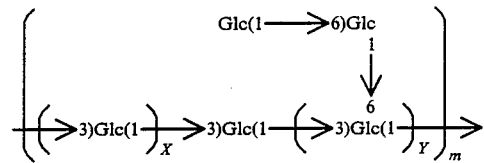

where X, Y, X' and Y' are 1 or larger integers, where X+Y and X'+Y' are integers in the range of from 3 to 5, and where m:n is from 1:3 to 1:5.

3. A food product containing the composition of claim 1.

* * * * *